United States Patent [19]
Mazzara et al.

[11] Patent Number: 5,631,154
[45] Date of Patent: May 20, 1997

[54] SELF ASSEMBLED, DEFECTIVE, NON-SELF-PROPAGATING LENTIVIRUS PARTICLES

[75] Inventors: Gail P. Mazzara, Winchester; Dennis L. Panicali, Acton; Bryan Roberts, Cambridge; Linda R. Gritz, Somerville, all of Mass.; Virginia Stallard, Sequim, Wash.; Anna Mahr, Natick, Mass.

[73] Assignee: Therion Biologics, Incorporated, Cambridge, Mass.

[21] Appl. No.: 18,344

[22] Filed: Feb. 16, 1993

Related U.S. Application Data

[63] Continuation of Ser. No. 580,538, Sep. 11, 1990, abandoned, which is a continuation-in-part of Ser. No. 540,109, Jun. 19, 1990, abandoned, which is a continuation-in-part of Ser. No. 360,027, Jun. 1, 1989, abandoned, which is a continuation-in-part of Ser. No. 205,454, Jun. 10, 1988, abandoned.

[51] Int. Cl.$^6$ .................. C12N 15/86; C12N 15/63; A61K 39/21; C07K 14/155
[52] U.S. Cl. .................. 435/236; 435/69.1; 435/69.3; 435/172.3; 435/320.1; 930/221
[58] Field of Search ................. 435/172.3, 236, 435/320.1, 69.1, 69.3; 930/221

[56] References Cited

U.S. PATENT DOCUMENTS 4,603,112  7/1986  Paoletti et al. .................. 435/235.1

FOREIGN PATENT DOCUMENTS

| 284416 | 9/1988 | European Pat. Off. . |
| 308220 | 3/1989 | European Pat. Off. . |
| 314569 | 5/1989 | European Pat. Off. . |
| WO8702038 | 4/1987 | WIPO . |
| WO8706258 | 10/1987 | WIPO . |
| WO8802022 | 3/1988 | WIPO . |
| WO8803562 | 5/1988 | WIPO . |
| WO8803563 | 5/1988 | WIPO . |
| WO/89/03429 | 4/1989 | WIPO . |
| WO89/07644 | 8/1989 | WIPO . |

OTHER PUBLICATIONS

M.E. Perkus et al (1985) Science 229: 981–984.
R. Mann et al (1983) Cell 33: 153–159.
A. Lever et al. (1989) J. Virol. 63: 4085–4087.
G. Franchini et al (1987) Nature 328: 539–543.
D.B. Boyle and E.H. Coupar, Virus Research 10:343–356 (1988).
J. Taylor, et al., Vaccine, 6:497–503 (1988).
J. Taylor, et al., Vaccine, 6:504–508 (1988).
D.B. Boyle and B.E.H. Coupar, J. Gen. Virol., 67:1591–1600 (1986).
D.B. Boyle, et al. Virology, 156:355–365 (1987).
F. Tomley, et al., J. Gen. Virol., 69:1025–1040 (1988).
M.M. Binns, et al., Virology, 170:288–291 (1989).
J. Taylor, et al., Technological Advances in Vaccine Development, (1988), L. Lasky (Ed.), Alan R. Liss, Inc., New York, pp. 321–334.
M.M. Binns, et al. Israeli J. Vet. Med., 42:124–127 (1986).
G. Rautmann, et al., AIDS Res. Hum. Restroviruses, 5:147–157 (1989).
C.D. Gowda, et al., J. Virol., 63:1451–1454 (Mar. 1989).
G. Mazzara, et al., Modern Approaches to Vaccines, Cold Spring Harbor Laboratory, New York, (1987).
G. Gheysen, et al., Modern Approaches to New Vaccines, Cold Spring Harbor Laboratory, New York, Sep. 14–18, Abstract No. 72 (1989).
D. Gheysen, et al. Cell, 59:103 (1989).
Smith, et al., J. Virol., 64:2743–2750 (1990).
J.W. Wills, Nature, 340:323–324 (1989).
T. Shioda and H. Shibuta, Virology, 175:139–148 (1990).
O. Haffar, et al., J. Virol., 64:2653–2659 (Jun. 1990).
V. Karacostas, et al., Proc. Natl. Acad. Sci. USA, 86:8964–8967 (Nov. 1989).
M. Delchambre, et al. The EMBO J., 8:2653–2660 (1989).
Haffar et al., J. Virol. 64(6):2653–2659 (1990).

*Primary Examiner*—Mindy Fleisher
*Assistant Examiner*—Johnny F. Railey II
*Attorney, Agent, or Firm*—Sewall P. Bronstein; Ronald I. Eisenstein; David S. Resnick

[57] ABSTRACT

Recombinant avipox viral vectors which express heterologous polypeptides capable of assembling into defective nonself-propagating viral particles are disclosed. The recombinant avipox viruses can be used to produce significant amounts of the heterologous polypeptides in avian or non-avian cells. Preferably, the recombinant avipox virus is a fowlpox virus. The viral particles can also be used as immunogens and for targeted delivery of heterologous gene products and drugs.

12 Claims, 2 Drawing Sheets

SELF ASSEMBLED, DEFECTIVE, NON-SELF-PROPAGATING LENTIVIRUS PARTICLES

RELATED APPLICATION

This is a continuation of application Ser. No. 07/580,538 filed on Sep. 11, 1990, now abandoned, which is a Continuation-in-part of U.S. Ser. No. 07/540,109, filed Jun. 19, 1990, now abandoned, which is a Continuation-in-part of U.S. Ser. No. 07/360,027, filed Jun. 1, 1989, now abandoned, which is a Continuation-in-part of U.S. Ser. No. 07/205,454, filed Jun. 10, 1988, now abandoned. The teachings of each application are incorporated herein by reference.

BACKGROUND

Recombinant approaches have been used in attempts to develop vaccines against diseases for which no vaccine currently exists, or for which conventional vaccine approaches are less desirable. For example, since the human immunodeficiency virus (HIV) was first identified as the etiologic agent of Acquired Immunodeficiency Disease Syndrome (AIDS), (Barre-Sinoussi et al. *Science* 220:868 (1983); Levey et al., *Science* 225:840 (1984); Gallo et al., *Science* 224:500 (1984)), considerable effort has been directed towards the development of a safe and effective vaccine.

The human immunodeficiency viruses, HIV-1 and HIV-2, are members of the lentivirus subclass of retroviruses. Gonda et al., *Science* 227:173 (1985); Sonigo et al., *Cell* 42:369 (1985). The virus particles contain an inner core comprised of capsid proteins (encoded by the viral gag gene) that encase the viral RNA genome. Rabson & Martin, *Cell* 40:477 (1985). The central core is surrounded by a lipid envelope that contains the viral-encoded envelope glycoproteins. Virus-encoded enzymes required for replication, such as the reverse transcriptase and integrase (encoded by the pol gene), are also incorporated into the virus particle.

Simian immunodeficiency virus (SIV) is a virus closely related to HIV. Several isolates of SIV have been cloned and sequenced. The results reveal 40–50% overall identity in the predicted amino acid sequences when compared to HIV-1 and about 75% when compared to HIV-2. Experimental inoculation of this virus into macaque monkeys has consistently resulted in long-term persistent infection, with most inoculated animals dying of a disease similar to AIDS in humans. A number of researchers have reported successful vaccination of macaques with whole inactivated SIV with protection against subsequent challenge with lethal doses of SIV (Desrosiers et al., *Proc. Natl. Acad. Sci. USA*, 86:6353 (1989); Murphey-Corb et al., *Science*, 246:1293 (1989)).

There are obvious difficulties with the use of whole virus for an HIV vaccine. The fear that an attenuated virus could revert to virulence, and the danger of incomplete inactivation of killed virus preparations, together with the reluctance to introduce the HIV genome into seronegative individuals have argued against the uses of live attenuated or killed HIV vaccines for the prevention of infection.

Advances in recombinant DNA technology may make it possible to use heterologous expression systems for the synthesis not only of individual antigens, but also of defective, nonself-propagating, virus-like particles. It has been demonstrated that capsid proteins of certain viruses can assemble into particles morphologically and immunologically similar to the corresponding virus. For example, the P1 precursor of several picornaviruses synthesized in vitro can be processed into individual capsid proteins which then assemble into immunoreactive virion-like particles. Nicklin et al., *Biotechnology* 4:33 (1986; Palmenberg et al., *J. Virol.* 32:770 (1979); Shih et al., *Proc. Natl. Acad. Sci. USA* 75:5807 (1978); Hanecak et al., *Proc. Natl. Acad. Sci. USA* 79:3973 (1982); Grubman et al., *J. Virol.* 56:120 (1985). Self-assembly of capsid proteins expressed in vivo in several recombinant expression systems has also been reported. For example, when human hepatitis B surface antigen is expressed in yeast cells, the polypeptide assembles into particles similar in appearance to those isolated from human plasma (Valenzuela et al., *Nature* 298:347 (1982)); these particles stimulate anti-hepatitis B antibody production in several species and can protect chimpanzees from virus challenge. McAleer et al., *Nature* 307:178 (1984).

In another example, it was shown that coexpression of canine parvovirus (CPV) capsid proteins VP1 and VP2 in murine cells transformed with a bovine papilloma virus/CPV recombinant plasmid resulted in the formation of self-assembling virus-like particles that resembled, biochemically and immunologically, authentic CPV virions (Mazzara et al., 1986, in *Modern Approaches to Vaccines*, Cold Spring Harbor Laboratory, N.Y.; R. M. Chanock and R. A. Lerner, eds. pp. 419–424; Mazzara et al., U.S. patent application No. 905,299, filed Sep. 8, 1986). When used to vaccinate susceptible dogs, these empty capsids elicited immune responses capable of protecting against CPV challenge. It has also been shown that the HIV-1 or SIV p55gag precursor polypeptide expressed in insect cells using the baculovirus expression system results in the formation of immature, retroviral-like particles that are secreted into the cell culture medium of infected cells. Gheysen et al., *Cell* 59:103 (1989); Delchambre et al., *The EMBO J.* 8:2653–2660 (1989).

In mammalian cells, HIV-like particles that contained core polypeptides as well as reverse transcriptase were produced after transient expression of the HIV gag-pol genes using an SV40 late replacement vector (Smith et al., *J. Virol.* 64:2653–2659 (1990). Mammalian cells infected with recombinant vaccinia virus containing the HIV gag-pol genes have also been shown to produce defective,.HIV-like particles (Karacostas et al., *Proc. Natl. Acad. Sci. USA*, 86:8964 (1989)).

Recombinant fowlpox virus (FPV) has also been used as a vector for the expression of foreign genes. Fowlpox virus is an avipox virus distantly related to vaccinia virus, an orthopox virus. Recombinant fowlpox viruses containing foreign DNA within a region of the viral genome which is nonessential for growth in tissue culture have been described by Boyle et al. International Patent Application PCT/AU87/00323, Boyle and Coupar (1988) *Virus Res.* 10:343. Vaccinia virus promoters are used to express the DNA in FPV.

Several other groups have published the construction of FPV recombinantso Noboru et al., (EPO 284,416, filed Mar. 25, 1988) disclose a number of genomic insertion sites which are nonessential for FPV growth in tissue culture, using the *E. coli* lacZ gene under the control of a vaccinia promoter. Paoletti (PCT/US88/02816, filed Aug. 24, 1988; Taylor et al., (1988) *Vaccine* 6: 497–503, 504–508) describes vectors for producing FPV recombinants using various vaccinia promoters for the expression of genes encoding foreign antigens, including the rabies G protein, turkey influenza hemagglutinin and avian bronchitis virus spike protein. Drillien and Spehner (EPO 314,569, filed Oct. 26, 1988) disclose the construction of FPV recombinants containing a gene encoding the measles F protein under the control of a vaccinia promoter.

Productive fowlpox infection is restricted in vivo to avian species and in vitro to cells derived from avian species.

Fowlpox virus does cause cytotoxic effect in mammalian cells (Burnett and Frothingham, *Archiv fur die gesamte Virusforschung*, 24:137 (1968)). The cytotoxic effect was not visible until three days post-infection with fowlpox virus and maximal effect was not observed until seven to nine days post infection. Pretreatment of fowlpox virus with ultraviolet light reduced the cytotoxic effect. These observations, i.e., the delayed onset of cytotoxic effect and the inhibitory effect of ultraviolet light, indicate that the cytotoxic effect of fowlpox virus in mammalian cells is not due to a previously synthesized toxic factor carried in with the infecting fowlpox virion, but is more likely due to de novo production of fowlpox viral material in the infected mammalian cell. Thus, these studies imply that a certain level of fowlpox viral gene expression may be occurring in mammalian cells, without production of infectious material. More recently, Paoletti (PCT/US88/02816, filed Aug. 24, 1988) and Taylor et al., (*Vaccine*, 6:497–503 (1988) confirmed that fowlpox viral gene expression occurs in infected non-arian cells. Native fowlpox gene expression was not investigated, but expression of foreign genes under the control of a vaccinia promoter was demonstrated in monkey or human cells infected with recombinant fowlpox virus containing these sequences. The techniques used to detect such foreign protein synthesis (e.g., radioimmunoprecipitation) are very sensitive and can therefore detect very low levels of gene expression. It is thus not clear whether quantitatively useful amounts of protein were made, for example, to be able to use fowlpox infection of mammalian cells for protein production. Sufficient protein was made to elicit a protective immune response against several pathogens. However, in many cases, especially in the case of rabies G protein, very low levels of antigen are needed to elicit a protective immune response.

SUMMARY OF THE INVENTION

This invention pertains to recombinant avipox viral vectors and preferably recombinant fowlpox viral vectors which express, in either avian or non-arian eukaryotic cells, at least one heterologous viral polypeptide capable of self-assembly, in vivo or in vitro, into defective, nonself-propagating viral particles, and to methods of producing the recombinant fowlpox virus (FPV). Preferably, the viral particles are produced by recombinant fowlpox virus that coexpress the env and gag-pol genes of lentiviruses such as HIV, SIV or feline immunodeficiency virus (FIV).

This invention also pertains to intermediate DNA vectors which recombine with a parent FPV in vivo or in vitro to produce the recombinant FPV vector, to methods of producing heterologous protein, and to methods of vaccinating a host with the recombinant viral vector to elicit protective immunity against the correlate heterologous pathogenic virus. In addition, this invention pertains to the synthesis of defective, nonself-propagating viral particles, such as lentivirus particles, produced by recombinant FPV in eukaryotic cells, in quantities sufficient for producing particles suitable for administration to humans or animals. These viral particles may be isolated and used alone as immunogens or in combination with other immunogens for vaccination against pathogenic viruses or for therapeutic purposes such as enhancing immune responses in an infected individual. Such fowlpox recombinants or the resulting particles may be used as targets to assess the humoral or cell-mediated immune response to an immunogen. The viral particles of this invention can also be used for targeted delivery of therapeutic agents, such as cytotoxic drugs or nucleic acids to specific cell types.

DETAILED DESCRIPTION OF THE INVENTION

Figure 1:
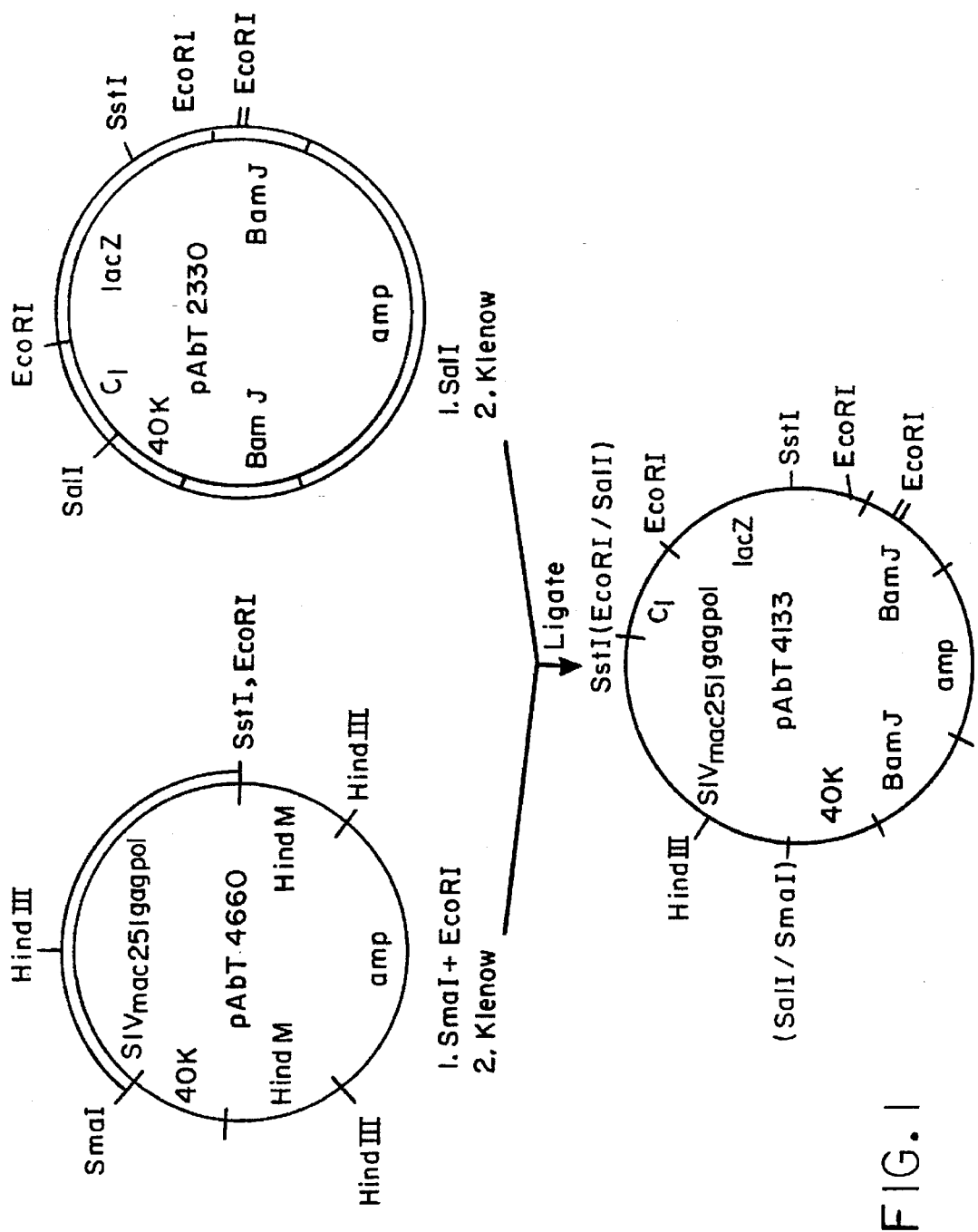
FIG. 1 shows the construction of plasmid pAbT4133 containing the $SIV_{MAC251}$ gag-pol gene under the control of the vaccinia virus 40K promoter.
Figure 2:
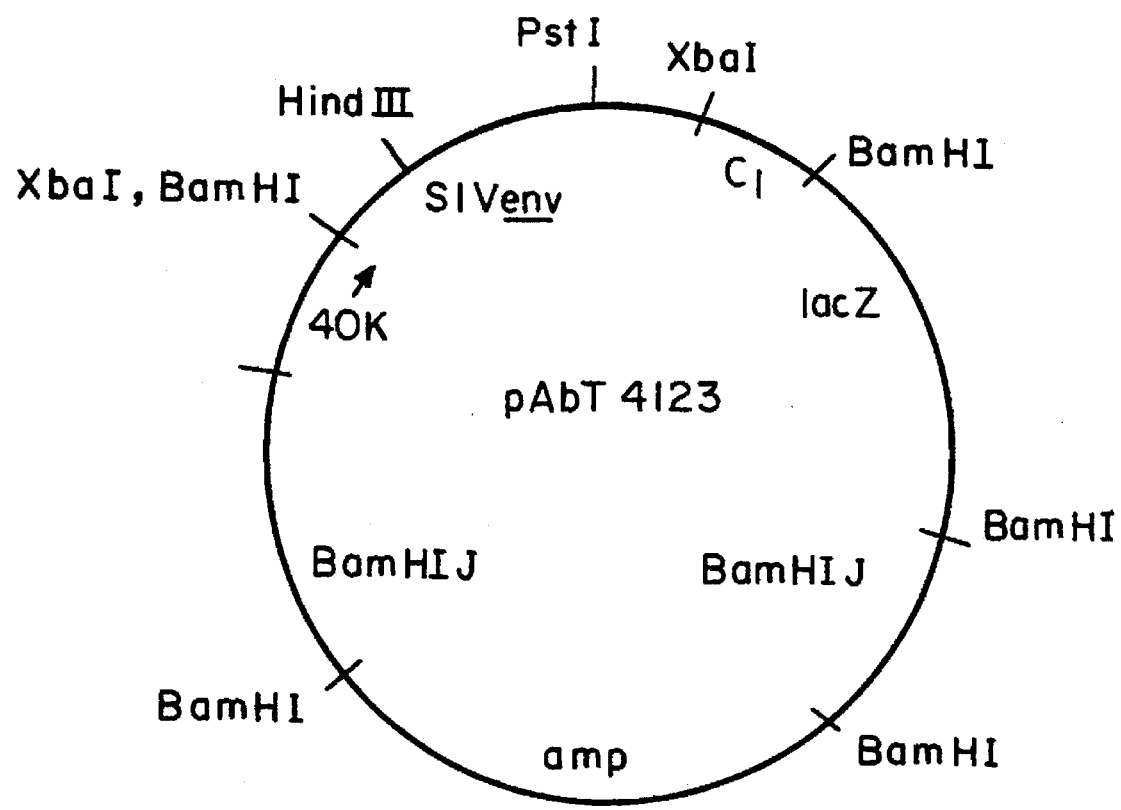
FIG. 2 shows plasmid pAbT4123 containing the $SIV_{MAC251}$ env gene under the control of the 40K promoter.

The invention pertains to recombinant avipox viruses and preferably recombinant fowlpox viruses capable of expressing, in eukaryotic cells, at least one gene encoding heterologous viral polypeptide(s). The expressed polypeptide(s) are capable of self-assembly into defective, nonself-propagating viral particles.

Preferably, the viral particles will contain retroviral envelope and core polypeptides, such as those from human immunodeficiency virus, simian immunodeficiency virus and feline immunodeficiency virus, all of which are members of the lentivirus subclass of retroviruses. The viral particles can have substantially little or no RNA packaged within the particle; or they can contain specific RNA for delivery of heterologous genes to a targeted cell. Methods for producing such viral particles have been described in U.S. application Ser. No. 07/540,109, filed Jun. 19, 1990, which corresponds to WO90/19803 the entire teachings of which are incorporated herein by reference.

The methods of producing viral particles, recombinant fowlpox viruses expressing these particles and uses therefor will be discussed in detail below and in the Examples.

1. Genes encoding viral antigens

Genes encoding viral polypeptides capable of self assembly into defective, nonself-propagating viral particles can be obtained from the genomic DNA of a DNA virus or the cDNA of an RNA virus or from available subgenomic clones containing the genes. These genes will include those encoding viral capsid proteins (i.e., proteins that comprise the viral protein shell) and, in the case of enveloped viruses, such as retroviruses, the genes encoding viral envelope glycoproteins. Additional viral genes may also be required for capsid protein maturation and particle self-assembly. These may encode, for example, viral proteases responsible for processing of capsid protein.

As an example, the genomic structure of picornaviruses has been well characterized, and the patterns of protein synthesis leading to virion assembly are clear. Rueckert, R. in *Virology* (1985), B. N. Fields et al. (eds.) Raven Press, New York, pp 705–738. In picornaviruses, the viral capsid proteins are encoded by an RNA genome containing a single long reading frame, and are synthesized as part of a polyprotein which is processed to yield the mature capsid proteins by a combination of cellular and viral proteases. Thus, the picornavirus genes required for capsid self-assembly include both the capsid structural genes and the viral proteases required for their maturation.

Another virus class from which genes encoding self-assembling capsid proteins can be isolated is the lentiviruses, of which HIV, SIV and FIV are examples. Like the picornaviral capsid proteins, the HIV gag protein is synthesized as a precursor polypeptide that is subsequently processed, by a viral protease, into the mature capsid polypeptides. However, the gag precursor polypeptide can self-assemble into virus-like particles in the absence of protein processing. Gheysen et al., *Cell* 59:103 (1989); Delchambre et al., *The EMBO J.* 8:2653–2660 (1989). Unlike picornavirus capsids, HIV and SIV capsids are surrounded by a loose membranous envelope that contains the viral glycoproteins. These are encoded by the viral env gene.

The examples illustrate the use of the $SIV_{MAC251}$ gag-pol or $SIV_{MAC}251$env gene selected for expression in recombinant fowlpox viruses of this invention. The SIV genes and their protein products are outlined in Table 1. The three major virion components derived from the env, gag, and pol genes are synthesized as precursor polyproteins which are subsequently cleaved to yield mature polypeptides as outlined in Table 1.

TABLE 1

SIV Genes for Recombination into Pox Virus

| Gene | Gene Product | | Processed Peptides |
|---|---|---|---|
| env | gp160 | gp120 | extracellular membrane protein |
|  |  | gp32 | transmembrane protein |
| gag | p55 | p27 | capsid proteins |
|  |  | p15 |  |
|  |  | p9 |  |
| pol | p160* | p10 | protease |
|  |  | p66/p51 | reverse transcriptase |
|  |  | p34 | endonuclease |

*Part of the gag-pol product.

2. Parent Viruses

A number of viruses, including retroviruses, adenoviruses, herpesviruses and pox viruses, have been developed as live viral vectors for the expression of heterologous antigens. Cepko et al., Cell 37: 1053–1062 (1984); Morin et al., Proc. Natl. Acad. Sci. USA 84:4626–4630 (1987); Lowe et al., Proc. Natl. Acad. Sci. USA 84:3896–3900 (1987); Panicali & Paoletti, Proc. Natl. Acad. Sci. USA 79: 4927–4931 (1982); Mackett et al., Proc. Natl. Acad. Sci. USA 79:7415–7419 (1982). The examples given illustrate the use of the pox virus family.

A preferred pox virus is fowlpox virus, a pathogen of poultry. This virus has also been developed into a eukaryotic cloning vector. Boyle et al., PCT applications WO88/02022 published Sep. 22, 1987 and WO89/07644 published Aug. 24, 1989; Yanagida et al., EP284416 published Sep. 28, 1988; U.S. patent application Ser. No. 07/398,762, filed Aug. 25, 1989 which corresponds to WO90/02191. Fowlpox virus (FPV) is the archetypal member of the arian poxviruses and the causative agent of pox in poultry (Woodruff, A. M. and E. W. Goodpasture (1931) Am. J. Pathol. 7:209–222; Woodruff, C. E. and E. W. Goodpasture (1929) Am. J. Pathol. 5:1–10; Woodruff, C. E. and E. W. Goodpasture (1930) Am. J. Pathol. 6:713–720. Pox of birds is prevale. nt world-wide but is not considered a public heath problem since the host-range of the avian poxviruses is limited to birds and excludes mammals (Tripathy, D. N. and G. H. Cunningham (1984) Arian Pox, Chapter 23, pp. 524–534, in Diseases of Poultry, 8th ed. M. S. Hofstad ed.).

Another preferred pox virus is vaccinia virus, a relatively benign virus which has been used for years as a vaccine against smallpox. Vaccinia virus has been developed as an infectious eukaryotic cloning vector (Paoletti and Panicali, U.S. Pat. No. 4,603,112) and recombinant vaccinia virus has been used successfully as a vaccine in several experimental systems. The virus is considered nononcogenic, has a well-characterized genome, and can carry large amounts of foreign DNA without loss of infectivity. Mackett, M. and G. L. Smith, J. Gen. Virol. 67:2067 (1986).

3. DNA vectors for in vivo recombination with a parent virus

According to the method of this invention, viral genes that code for polypeptides capable of assembly into viral particles are inserted into the genome of FPV in such a manner as to allow them to be expressed by that virus along with the expression of the normal complement of FPV proteins. This can be accomplished by first constructing a DNA donor vector for in vivo recombination with FPV.

In general, the FPV donor vector contains the following elements:

a) a prokaryotic origin of replication, so that the vector may be amplified in a prokaryotic host;

b) a gene encoding a marker which allows selection of prokaryotic host cells that contain the vector (e.g., a gene encoding antibiotic resistance);

c) at least one heterologous viral gene (e.g., HIV, SIV or FIV genes), each gene located adjacent to a transcriptional promoter (e.g., FPV $C_1$ or $C_2$ promoters; vaccinia 7.5K, 30K, 40K, 11K or BamF promoters, or modified versions of these promoters) capable of directing the expression of adjacent genes; and d) DNA sequences homologous to the region of the FPV genome where the foreign gene(s) will be inserted, flanking the construct of element c (e.g., the BamHI J fragment of FPV).

Other fowlpox promoters and insertion sites are described in detail in U.S. Ser. No. 07/398,762, filed Aug. 25, 1989, which corresponds to WO90/02191 the entire teachings of which are incorporated herein by reference.

Methods for constructing donor plasmids for the introduction of multiple foreign genes into pox virus are described in U.S. patent application Ser. No. 910,501, filed Sep. 23, 1986, which corresponds to EP 026/940 entitled "Pseudorabies Vaccine", the techniques of which are incorporated herein by reference. In general, all viral DNA fragments for construction of the donor vector, including fragments containing transcriptional promoters and fragments containing sequences homologous to the region of the parent virus genome into which foreign genes are to be inserted, can be obtained from genomic DNA or cloned DNA fragments.

The donor vector preferably contains an additional gene which encodes a selectable marker under control of a separate promoter which will allow identification of recombinant viruses containing inserted foreign DNA. Several types of marker genes can be used to permit the identification and isolation of recombinant viruses. These include genes that encode antibiotic or chemical resistance (e.g., see Spyropoulos et al., J. Virol. 62:1046 (1988); Falkner and Moss., J. Virol. 62:1849 (1988); Franke et al., Mol. Cell. Biol. 5:1918 (1985)), as well as genes, such as the E. coli lacZ gene, that permit identification of recombinant viral plaques by colorimetric assay. Panicali et al., Gene 47:193–199 (1986).

4. Integration of foreign DNA sequences into the FPV genome and isolation of recombinants Homologous recombination between donor plasmid DNA and viral DNA in an infected cell results in the formation of recombinant fowlpox viruses that incorporate the desired elements. Appropriate host cells for in vivo recombination are generally avian cells, such as chick embryo fibroblasts, that can be productively infected by the virus and transfected by the plasmid vector. Infection of cells with pox virus and transfection of these cells with plasmid vectors is accomplished by techniques standard in the art (Cohen and Panicali, U.S. Ser. No. 07/398,761, Filed Aug. 25, 1989 which corresponds to WO90/02191; Panicali and Paoletti, U.S. Pat. No. 4,603,112).

Following in vivo recombination, recombinant viral progeny can be identified by one of several techniques. The presence of integrated foreign DNA can be detected by hybridization with a labeled DNA probe specific for the inserted DNA. Preferred techniques for selection, however, are based upon co-integration of a gene encoding a marker or indicator gene along with the gene of interest, as described above. A preferred indicator gene is the *E. coli* lacZ gene which encodes the enzyme beta-galactosidase. Selection of recombinant FPV expressing beta-galactosidase can be done by employing a chromogenic substrate for the enzyme. For example, recombinant viruses are detected as blue plaques in the presence of the substrate 5-bromo-4-chloro-3-indolyl-beta-D-galactoside or other halogenated-indolyl-beta-D-galactosides (e.g. BluoGal™).

Another method by which recombinant viruses containing genes of interest can be identified is by an in situ enzyme based immunoassay in which protein expressed by these genes in fowlpox-infected cells is detected by the formation of live black plaques.

As described more fully in the Examples, donor plasmids containing the SIV$_{MAC251}$ gag-pol or env gene were recombined into FPV at the BamHI J region and recombinant fowlpox viruses were selected as described above.

5. Characterizing the viral antigens expressed by recombinant fowlpox viruses

Once a recombinant FPV has been identified, a variety of methods can be used to assay the expression of the polypeptide encoded by the inserted gene. These methods include black plaque assay (an in situ enzyme immunoassay performed on viral plaques), Western blot analysis, radioimmunoprecipitation (RIPA), and enzyme immunoassay (EIA). Antibodies to antigens expressed by viral pathogens are either readily available, or may be made according to methods known in the art. For example, for human immunodeficiency virus, the antibodies can be either sera from human patients infected with HIV, or commercially available monoclonal antibodies directed against specific HIV polypeptides. These assays can be performed on arian cells such as chick embryo fibroblasts or on non-avian cells such as BSC-40 cells (monkey kidney).

6. Viral particle formation

Expression analysis described in the preceding section can be used to confirm the synthesis of the polypeptides encoded by inserted heterologous viral genes, but does not address the question of whether these polypeptides self-assemble, in vivo or in vitro, into defective viral particles. Two experimental approaches can be used to examine this issue.

The first approach is to visually examine by electron microscopy lysates of eukaryotic cells infected with recombinant fowlpox viruses that express one or more viral polypeptides. The presence of retroviral envelope glycoproteins on the surface of the particles can be demonstrated with immunogold electron microscopy, using a monoclonal antibody directed against one of the envelope glycoproteins.

In order to characterize the defective viral particles produced by recombinant fowlpox viruses expressing viral polypeptides, these particles can be isolated by high speed centrifugation from the culture medium of cells infected with the recombinant viruses in the presence of [$^{35}$S]-methionine. The pellet resulting from centrifugation of the culture medium can be resuspended and both the pellet and the supernatant can be immunoprecipitated with an appropriate antiserum to analyze the viral polypeptides present in each fraction. For example, in the case of recombinants expressing SIV polypeptides, macaque anti-SIV antisera (for fowlpox/SIV recombinants) can be used for the analysis.

To further characterize the material in the pellet resulting from centrifugation of the culture medium, the pellet can be resuspended and analyzed on a sucrose gradient. The gradient can then be fractionated and the fractions immunoprecipitated with the appropriate antiserum. These experiments show whether the pellet contains material banding at the density expected for defective viral particles.

These methods can also be used to determine whether envelope proteins are assembled onto these particles. For example, these experiments can be performed using eukaryotic cells coinfected in vitro with one FPV recombinant expressing gag and a second FPV recombinant expressing env. The simultaneous expression in a single cell of both env and gag polypeptides, whether directed by a single divalent recombinant virus or by two different monovalent viruses, would be expected to result in the formation of defective retroviral particles that contain a protein core comprising gag-encoded polypeptides surrounded by an envelope containing virally-encoded envelope glycoproteins.

7. Vaccines

The defective virus particles produced by the recombinant fowlpox viruses can be isolated from eukaryotic cells infected in cell culture with the recombinant viruses and from the culture medium of these infected cells, and used for vaccination of individuals susceptible to viral infection. If non-avian cells are used, purification of the particles is simplified due to the absence of mature fowlpox virions contaminating the heterologous particles.

The defective particles resemble the native virus, but will not contain infectious viral genetic material, such as HIV mRNA. Consequently, they offer the advantage of conventional killed virus vaccine preparations, yet circumvent the major drawbacks to the use of killed virus as a vaccine for the prevention of infection. These include the danger of incomplete inactivation of killed virus preparations and, as for the case of certain viruses, such as retroviruses, the reluctance to introduce a complete viral genome (the HIV genome, for example) into seronegative individuals.

Vaccine compositions utilizing these defective virus particles would generally comprise an immunizing amount of the viral particles in a pharmaceutically acceptable vehicle. The vaccines would be administered in a manner compatible with the dosage formulation, and in such amount as would be therapeutically effective and immunogenic.

Finally, the purified particles may be used in combination with live recombinant viruses as part of a total vaccination protocol, either as the primary immunizing agent, to be followed by vaccination with live recombinant virus, or to boost the total immune response after primary vaccination with live recombinant virus.

8. Therapeutic use of defective viral particles produced b$_E$ recombinant avipox viruses expressing viral antigens capable of assembling into defective viral particles Even if immunization cannot protect against initial infection, immunization of a previously infected individual might, for certain viruses, sufficiently boost immunity to protect against the onset of disease. This is, for example, how rabies vaccine is used therapeutically. Alternatively, for viruses that establish latency, immunization of an infected individual might prolong the latency period of that virus within the individual. (Salk, *Nature*, 327: 473–476 (1987)). This may be particularly important in the case of viral infections characterized by long latency periods, such as immunodeficiency virus or herpesvirus infections.

The defective viral particles of this invention can also be used to deliver heterologous genes (e.g., antisense genes, genes encoding toxins, genes encoding an immunogen) to a targeted cell. Methods for producing such viral particles have been described in U.S. application Ser. No. 07/540,109, filed Jun. 19, 1990 which correspond to WO91/19803, the teachings of which are incorporated herein by reference. Viral particles could be used to deliver mRNAs that are directly translated in the target cell into the encoded protein product. Alternatively, specific RNA packaged within retroviral particles that contain active reverse transcriptase and other pol-encoded functions could be delivered to the targeted cells and reverse transcribed into DNA. This DNA could then integrate into the host genome, and the encoded genes would be expressed by host transcription/translation machinery. These approaches could be used to deliver genes encoding products toxic to the targeted cells (e.g., virally infected cells). In another application, particles containing RNA encoding heterologous genes could be administered to an individual in order to elicit immune responses to the encoded gene products.

9. Therapeutic use of defective virus particles as agents for targeted drug delivery Defective, nonself-propagating virus particles can also be used to deliver certain drugs (e.g. cytotoxic drugs, antiviral agents, nucleic acids) to virus receptor-bearing cells. Such drugs may be coupled, by techniques known in the art, to the outer surface of the virus particle, or incorporated within, and delivered with high specificity to target cells. For example, cytotoxic drugs may be coupled to defective immunodeficiency virus particles and delivered with a high degree of specificity to $CD4^+$ T cells, since the immunodeficiency virus envelope glycoprotein present on these particles binds specifically and with high affinity to the CD4 molecule. Similarly, poliovirus particles, for example, preferentially bind cells of the nasopharynx and gut, and thus can be used to direct delivery of specific agents to these or other cells that have poliovirus receptors.

Specific targeting of therapeutic agents can be achieved by selecting as the heterologous glycoprotein one with a tropism for surface receptors on specific cell types. For example, viral particles containing herpesvirus glycoproteins might be used to target cells of the nervous system, whereas viral particles containing the hepatitis B surface antigen would target hepatic cells.

This invention is illustrated further by the following examples:

EXAMPLES

MATERIALS AND METHODS

Cells

Primary chicken embryo fibroblast (CEF) and chicken embryo dermal (CED) cells were prepared by published procedures (Rein, A., and H. Rubin (1968) *Exp. Cell Res.* 49:666; Silim, A., M. A. S. Y. El Azhary, and R. S. Roy (1982) *Avian Dis.* 26:182–185). The fibroblast cultures were maintained in Dulbecco's Modified Eagle Media (DME) supplemented with 10% calf serum (CS), and the dermal cells were maintained in Minimum Essential Media (MEM) containing 5% fetal calf serum (FCS). The fibroblast cultures were maintained for a maximum of 3 passages in tissue culture and the dermal cells for a maximum of 6 passages. All cells were grown at 37° C. and under 5% $CO_2$.

Virus Strains.

A FPV vaccine strain obtained from Schering-Plough and designated for research purposes only, was employed exclusively in these studies. The strain was plaque purified twice on both CEF and CED monolayers before use.

Amplification and Purification of FPV.

Viral stocks were prepared on CED monolayers by infection at a multiplicity of infection (moi) of 0.01 and replication was allowed to proceed for 5 days at 37° C. and 5% $CO_2$. Infected cells were scraped directly into the culture media and virus was released by multiple cycles of freezing and thawing.

The amplification of single plaque isolates was conducted by infection of $2\times10^6$ cells in a confluent monolayer with one-half of the plaque pick. After five days of replication, the progeny virus were harvested, released by multiple cycles of freezing and thawing, and one-third of that material was used to inoculate $1\times10^7$ cells. Amplification was again allowed to proceed for five days, and the resulting virus was harvested by scraping the cells into the culture media, and released by multiple cycles of freezing and thawing. A viral stock prepared in this fashion results in a stock containing approximately $1\times10^8$ pfu.

Partially purified virus was prepared, when necessary, by centrifugation by a procedure developed for the purification of vaccinia virus (Joklik, W. K. (1962) *Virology* 13:9–18).

Plaque Assay of FPV.

Plaque formation of FPV was accomplished on monolayers of CED cells which were seeded at a density of $2\times10^6$ cells per 60 mm tissue culture dish. Viral suspensions were allowed to adsorb to the cells in 1.0 ml of MEM containing 2% FCS for 90 minutes, and were removed by aspiration and replaced with 5.0 mls of 0.6% agarose containing DME and 2% CS. The plaques formed at 37° C. and 5% $CO_2$ were generally visible after 48 hours, and were stained for 12 to 48 hours with an additional agarose overlay containing 0.001% neutral red. The Beta-galactosidase ,activity following plaque formation was detected with an agarose overlay containing DME and 300 μg/ml of 5-bromo-4-chloro-3-indolyl-β-D-galactopyranoside (X-gal).

Conditions for the Formation of Recombinant FPV

Confluent monolayers of $2\times10^6$ CEF cells in 60 mm tissue culture dishes were infected at an moi of 0.1 for about 60 to 90 minutes in MEM containing 2% FCS. Following adsorption of the virus, the inoculum was removed and replaced with 5.0 ml of growth medium. Twenty μg of plasmid DNA in 500 μl of HEPES-buffered saline was precipitated from the buffer by the addition of 31 μl of 2M $CaCl_2$ at room temperature for 30 to 45 minutes. The precipitated plasmid DNA was added directly to the growth medium. Viral replication and recombination were allowed to proceed for an additional 72 hours. The viral progeny were harvested by scraping the CEF cells directly into the growth media, released by multiple cycles of freezing and thawing, and titered on confluent monolayers of CED cells.

Preparation of Viral Genomic DNA.

FPV genomic DNA was prepared by infecting a confluent monolayer of CED cells with FPV at an MOI of 10, incubating overnight at 39° C. until 100% CPE was observed. The infected cells were scraped directly into the growth medium and were harvested by centrifugation at 3000 rpm for 10 minutes in a clinical centrifuge. The supernatant was discarded and the cell pellet washed 3 times by resuspension in 10 ml of PBS and recentrifuged. The final washed cell pellet was resuspended in 1.8 ml of 10 mM Tris-Cl (pH7.8), 5 mM EDTA, and 10 mM KCl., and incubated on ice for about 10 minutes with intermittent vortexing. One μl of 2-mercaptoethanol and 200 μl of a solution of 10% Triton X-100 were added and the cells were lysed for an additional 10 minutes on ice with intermittent vortexing. Nuclei and large debris were removed by centrifugation at 2000 rpm for 10 minutes in a clinical centrifuge. This centrifugation was repeated one time. The supernatant containing the partially purified virus was treated at 37° C. for two hours with 10 μl of a 20 mg/ml solution of proteinase K in $H_2O$, 40 μl of 5M NaCl, and 100 μl of 10% SDS. The supernatant was then extracted twice with phenol/chloroform (1/1:v/v). The genomic DNA was then precipitated by the addition of one tenth the volume of 3M sodium acetate and 2 volumes of ethanol at −20° C. for about 30 minutes. The nucleic acid was collected by centrifugation at 12000 rpm for 10 minutes in a Sorvall SS-34 rotor, and, after drying, was resuspended in 50 μl of 10 mM Tris-Cl (pH 8.0), 1 mM EDTA.

Hybridization Anal%sis.

Viral genomic DNA was digested with restriction endonuclease BamHI for 4 hours and the resulting fragments were resolved on 1% agarose gels containing 40 mM Tris-acetate (pH8.0), 2 mM EDTA. The fragments were transferred to nitrocellulose and analyzed by hybridization to the appropriate radiolabelled DNA by standard procedure (Maniatis, T., E. F. Fritsch, and J. Sambrook (1982) *Molecular Cloning*, A Laboratory Manual).

Construction of Plasmids.

All manipulations, including plasmid isolation, restriction endonuclease digestion, agarose gel electrophoresis, fragment isolation, phosphatase treatment, use of linkers, ligation, and bacterial transformations were performed by standard published procedures (Maniatis, T., E. F. Fritsch, and J. Sambrook (1982) *Molecular Cloning*, A Laboratory Manual).

Metabolic Labeling.

CED cells were grown for 24 hr to a density of $10^6$ cells per 6 cm plate and then infected with FPV at an MOI of 10 for 120 min at 37° C. The cells were labeled with either $[^3H]$ glucosamine or $[^{35}S]$ methionine. When $[^{35}S]$ methionine was used, the labeling medium consisted of 9.5 ml of methionine-free DME, 4% FCS, 2 mM L-glutamine, 100 μl DME, 100 μCi $[^{35}S]$ methionine (New England Nuclear) and carrier methionine (0.3 mg/100 ml). When cells were labeled with $[^3H]$ glucosamine, the DME-4% FCS lacked leucine and was supplemented with 100 μCi $[^3H]$ glucosamine (New England Nuclear) and leucine (1.46 mg/100 ml). Cells were harvested after approximately 40 hr, washed twice with PBS and lysed by sonicating 3 times for 5 seconds, each time in 1 ml of immunoprecipitation buffer (IPB: 10 mM Tris-HCl, pH7.2, 650 mM NACl, 1% Triton X-100, 1% sodium deoxycholate, 0.1% SDS, 5 mM EDTA, 1 mM phenylmethylsulfonylfluoride (PMSF) and 0.1 mg/ml trypsin inhibitor), followed by centrifugation at 4000 RPM at 4° for 10 min. Lysates were stored at −80°.

Immunoprecipitation.

Immuniprecipitations were carried out on cell lysate samples each labeled with 1 μCi $[^{35}S]$ methionine in 0.2 ml of IPB or 1 μCi $[^3H]$ glucosamine in 0.25 ml of IPB. All incubations with antibodies were done with rocking at 4° C. Antiserum was added to the cell lysate and rotated at 4° for 2 hours or overnight. 50 μl of a 1:1 solution (v/v) of Protein A-sepharose in IPB was added to each sample. Samples were rotated for one additional hour at 4° C. Samples were washed four times with 1.0 ml of IPB at 4° C., centrifuging at 12,000 RPM for 15 seconds to pellet sepharose after each wash. Pellets were washed once with 1.0 ml of TBS (TBS: 10 mM Tris, 150 mM NACl, pH8.2) at 4° C. The washes were very important to reduce background from non-specific binding. The sepharose pellets were dried by inverting them over paper towels and allowing remaining liquid to run off. Pellets were resuspended in 20 μl of SDS gel sample buffer (Laemmli, (1970), *Nature* 227:680). The samples were vortexed vigorously and heated at 100° C. for 5 minutes. Samples were loaded on an SDS polyacrylamide gel which contained a 7% separation gel and a 3% stacking gel. The SDS polyacrylamide gel electrophoresis was carried out under reducing conditions and was followed by autoradiography.

Biochemical Analysis of Recombinant Fowlpox-directed Retroviral Particle Formation BSC-40 or CED cells infected with the wild-type or recombinant fowlpox virus were labeled with $[^{35}S]$-methionine, using the same labeling procedure used for immunoprecipitation analysis. After 24 hours, the medium from infected cells was collected and clarified twice by centrifugation at 1000 rpm for 5 minutes. The resulting supernatant was centrifuged at 24K for 90 minutes in an SW28 rotor. The supernatant was removed, and the resulting pellet was resuspended in 3 ml PBS buffer (136 mM NaCl, 2.7 mM KCl, 8.1 mM $Na_2HPO_4$, 1.5 mM $HK_2PO_4$). Samples from the supernatant and pellet were subjected to immunoprecipitation analysis, using macaque anti-SIV antiserum as described for immunoprecipitation analysis above.

Example 1

Production of defective SIV virus-like particles by avian or mammalian cells infected with recombinant fowlpox virus (FPX) expressing SIV gag-pol (FIG. 1)

For vaccinia virus, vaccinia vector pAbT4660 (American Type Culture Collection (ATCC) Accession No. 40866) was used to insert the $SIV_{MAC251}$ gag-pol gene into vaccinia virus strain vAbT33 to form vAbT394 using methods described in U.S. patent application Ser. No. 07/540,109 filed Jun. 19, 1990 which corresponds to WO91/19803. A sample of pAbT4660 was deposited with the American Type Culture Collection; 12301 Parklawn Drive; Rockville, Ma. on Aug. 8, 1990, and received ATCC Accession No. 40866. Production of SIV-like particles was demonstrated using methods described in U.S. patent application Ser. No. 07/540,109 filed Jun. 9, 1990 which corresponds to WO91/19803, the entire teachings of which are incorporated herein by reference.

Fowlpox recombination vector pAbT2330 (Cohen and Panicali, 1989, U.S. patent application Ser. No. 07/398,762 filed Aug. 25, 1989, which corresponds to WO90/02191, the entire teachings of which are incorporated herein by reference) was digested with SaiI and treated with Klenow and calf intestinal phosphataseo pAbT4660 was digested with SmaI and EcoRI, treated with Klenow and the 4800 bp fragment containing $SIV_{MAC251}$ gag-pol was gel-purified. The two fragments were ligated to form pAbT4133 as shown in FIG. 1. pAbT4133 is a vector for the insertion and expression of SIV gag and pol in FPV. pAbT4133 contains the SIV gag-pol gene under the control of the vaccinia virus 40K promoter, the *E. coli* lacZ gene under control of the FPV $C_1$ promoter (referred to as 2138 promoter in Cohen and Panicali, U.S. patent application Ser. No. 07/237,285 filed Aug. 26, 1988, which corresponds to U.S. Pat. No. 5,093,258) for selection of FPV recombinants, flanked by portions of the FPV BamHI J fragment for directing recombination into the FPV genome and a bacterial replicon and ampicillin-resistance gene for growth and selection in *E. coli*.

pAbT4133 was used as a vector to insert the SIV gag-pol gene into FPV by in vivo recombination using methods described previously (Cohen and Panicali, U.S. patent application Ser. No. 07/237,285 filed Aug. 26, 1988 which corresponds to U.S. Pat. No. 5,093,258). FVP recombinants, designated FPV74, were obtained and purified. Southern analysis of FPV genomic DNA, isolated as described for vaccinia virus, confirmed the presence of the SIV gag-pol gene inserted appropriately into the FPV BamHI J genomic region. Immunoprecipitation analysis using FPV74-infected chick embryo dermal (CED) cells labeled with [$^{35}$S] methionine and antisera from an SIV-infected macaque revealed the synthesis of gag and pol-encoded proteins of the expected sizes.

To determine whether SIV virus-like particles were produced by this recombinant, CED cells or BSC-40 cells were infected with FPV74 or vaccinia vAbT394 and labeled with [$^{35}$S] methionine. Immunoprecipitation analysis of the cell lysate, culture medium and fractionated medium (supernate and high speed pellet) were performed as described in U.S. patent application Ser. No. 07/205,454 filed Jun. 10, 1989 which corresponds to WO89/2095. The pelleted medium contains gag and pol proteins comparable to the vaccinia-produced capsid proteins, indicating that FPV74 produces SIV virus-like particles which are present in the medium of infected cells.

Example 2

Characterization of SIV virus-like particles in mammalian cells infected with recombinant FPV expressing SIV gag-pol Particles in the high-speed pellet were characterized further by centrifugation of the high-speed pellet from [$^{35}$S] methionine labeled FPV74-infected BSC-40 cells, through a 15–45% linear sucrose gradient with a 60% cushion. The gradient was collected in 15 fractions. A sample of each fraction was run on an SDS-PAGE gel. Results showed that the SIV gag and pol proteins were distributed through the gradient with the peak amount of protein running at 35% sucrose. This corresponds to the same size as the vaccinia-produced or native SIV capsids.

Fowlpox titers were assayed on each fraction. No labeled protein corresponding to FPV was observed consistent with the nonproductive nature of FPV infection of mammalian cells, but it was anticipated that residual virus which did not infect the cells would be present in the high-speed pellet. Titers were low as expected, and peaked two fractions lower than the capsid peak, as expected, since FPV is larger than SIV.

Electron microscopy of FPV74-infected cells revealed capsid structures budding from the surface of infected cells as seen with vaccinia/SIV-infected cells.

Example 3

Quantitation of SIV virus-like particle production in mammalian cells infected with recombinant FPV expressing SIV gag-pol A 15 cm plate containing $10^7$ BSC-40 cells was infected with FPV74 at an MOI of 5. Twenty-four hours post-infection, the culture medium was clarified twice by low speed centrifugation, then was centrifuged at 51,000×g for 90 minutes to pellet particulate material. This material was fractionated on a sucrose gradient as described in Example 2. A sample of each fraction was assayed for gag p27 protein using an SIV core antigen ELISA kit (SIV Core Ag Assay; Coulter Corp.). p27 protein was distributed throughout the gradient in the same manner as the labeled protein described in Example 2 with the peak amount of protein occurring at 35% sucrose. The total amount of p27 particle core antigen present in the pelleted material from the clarified culture medium was 7.2 micrograms per $10^7$ BSC-40 cells.

Example 4

Production of SIV-like particles containing env-encoded Protein in mammalian cells co-infected with recombinant FPV (FIG. 2)

The $SIV_{MAC251}$ env gene from pAbT4593 (U.S. Application Ser. No. 07/360,027 filed Jun. 1, 1989) was inserted into pAbT2330 to form pAbT4123 shown in FIG. 2. The same env gene could be obtained from a 2589 bp BamHI fragment of pAbT4585 (ATCC accession number 67729) and similarly inserted into the multiple cloning site of pAbT2330. pAbT4123 was used as a vector to insert the SIV env gene into FPV by in vivo recombination as described above. FPV recombinants designated FPV67 were obtained and purified. Southern analysis of FPV genomic DNA confirmed the presence of the SIV env gene inserted appropriately into the FPV BamHI J genomic region. Immunoprecipitation analysis using FPV67-infected chick embryo dermal (CED) cells labeled with [$^{35}$S] methionine and antisera from an SIV-infected macaque revealed the synthesis of env-encoded proteins of the expected sizes. A sample of plasmid pAbT4585 was deposited with the American Type Culture Collection; 12301 Parklawn Drive; Rockville, Md. on Jun. 10, 1988, and received ATCC Accession No. 67729.

A co-infection experiment was done with FPV74 (SIV gag-pol) and FPV67 (SIV env) to determine whether envelope proteins would be present on the capsids from co-infected BSC-40 cells. Immunoprecipitation analysis of the high speed pellet from gag-pol alone, env alone, or gag-pol plus env co-infections was performed. A low level of envelope protein was observed with env alone, which may be present in the high speed pellet due association with the cell membrane fragments present in the pellet. However, a much larger amount of envelope protein is observed in the high speed pellet of cells co-infected with FPV/SIV gag-pol indicating that env proteins are being assembled on particles. Electron microscopy of cells co-infected with FPV67 and FPV74 using immunogold staining with a monoclonal antibody against envelope protein confirmed the presence of envelope protein on the surface of particles.

A sample of plasmid pAbT2320, a fowlpox recombination vector, was deposited with the American Type Culture Collection; 12301 Parklawn Drive; Rockville, Ma. on Aug. 25, 1989, and received ATCC Accession No. 40647.

Equivalents

Those skilled in the art will recognize, or be able to ascertain using no more than routine experimentation, many equivalents to the specific embodiments of the invention described herein. Such equivalents are intended to be encompassed by the following claims:

We claim:

1. An avipox virus vector having inserted therein at least two DNA sequences from a single species of lentivirus, wherein one of the lentivirus DNA sequences is the env gene and the other of the lentivirus DNA sequences is selected from the group consisting of the gag gene and gag-pol gene, such that the lentivirus DNA sequences express either env and gag proteins, or express env and gag-pol proteins in a eukaryotic host cell co-infected with the two pox virus vectors, and the lentivirus proteins self-assemble into defective, non-self-propagating lentivirus particles.

2. Two avipox virus vectors, each avipox virus vector having inserted therein only one of either of two DNA sequences from a single species of lentivirus, wherein one of the lentivirus DNA sequences is the env gene and the other of the lentivirus DNA sequences is selected from the group consisting of the gag gene and gag-pol gene, such that the lentivirus DNA sequences express either env and gag proteins, or express env and gag-pol proteins in a eukaryotic host cell co-infected with the two pox virus vectors, and the lentivirus proteins self-assemble into defective, non-self-propagating lentivirus particles.

3. The avipox vector of claim 1, wherein the avipox is a fowlpox virus.

4. The avipox vectors of claim 2, wherein each avipox is a fowlpox virus.

5. The avipox vector of claim 3, wherein the lentivirus is Simian Immunodeficiency Virus (SIV) or Human Immunodeficiency Virus (HIV).

6. The avipox vectors of claim 4, wherein the lentivirus particle is Simian Immunodeficiency Virus (SIV) or Human Immunodeficiency Virus (HIV).

7. A self-assembled, defective non-self-propagating lentivirus particle produced by eukaryotic host cell infected with the avipox virus vector of claim 1.

8. A self-assembled, defective non-self-propagating lentivirus particle produced by eukaryotic host cell infected with the avipox virus vector of claim 2.

9. The avipox vector of claim 5 wherein the lentivirus is HIV.

10. The avipox vector of claim 6 wherein the lentivirus is HIV.

11. A self-assembled, defective non-self-propagating lentivirus particle produced by eukaryotic host cell infected with the avipox virus vector of claim 9.

12. A self-assembled, defective non-self-propagating lentivirus particle produced by eukaryotic host cell infected with the avipox virus vector of claim 10.

* * * * *